(12) United States Patent
Benner et al.

(10) Patent No.: US 9,445,941 B2
(45) Date of Patent: Sep. 20, 2016

(54) BIORESORBABLE DRUG ELUTING INTRAVITREAL IMPLANT SYSTEM AND METHOD

(71) Applicant: DRUG DELIVERY COMPANY, LLC, Salisbury, MD (US)

(72) Inventors: Jeffrey D. Benner, Salisbury, MD (US); Steven M. Cohen, Saint Petersburg, FL (US)

(73) Assignee: Drug Delivery Company, LLC, Salisbury, MD (US)

(*) Notice: Subject to any disclaimer, the term of this patent is extended or adjusted under 35 U.S.C. 154(b) by 0 days.

(21) Appl. No.: 14/511,337

(22) Filed: Oct. 10, 2014

(65) Prior Publication Data

US 2015/0133896 A1    May 14, 2015

Related U.S. Application Data

(60) Provisional application No. 61/901,099, filed on Nov. 7, 2013.

(51) Int. Cl.
*A61F 9/00* (2006.01)
*A61M 37/00* (2006.01)

(52) U.S. Cl.
CPC ............ *A61F 9/0017* (2013.01); *A61F 9/0008* (2013.01); *A61F 2210/0004* (2013.01); *A61M 37/0069* (2013.01); *A61M 2210/0612* (2013.01)

(58) Field of Classification Search
CPC ......... A61M 37/0069; A61M 5/3134; A61M 5/329; A61M 2210/0612; A61F 9/0026; A61F 9/0017; A61F 9/0008
See application file for complete search history.

(56) References Cited

U.S. PATENT DOCUMENTS

| | | | |
|---|---|---|---|
| 4,327,734 A | 5/1982 | White | |
| 4,351,337 A * | 9/1982 | Sidman | ............... A61K 9/0024 424/424 |
| 2005/0171504 A1 | 8/2005 | Miller | |
| 2011/0098686 A1 * | 4/2011 | Varner | .................. A61F 9/0017 604/890.1 |
| 2012/0083765 A1 * | 4/2012 | LaBelle | ................ A61F 9/0017 604/521 |
| 2013/0165860 A1 * | 6/2013 | Doud | .................... A61F 9/0017 604/117 |
| 2014/0031833 A1 | 1/2014 | Novakovic et al. | |
| 2014/0243795 A1 * | 8/2014 | Varner | .................. A61F 9/0017 604/521 |

OTHER PUBLICATIONS

Lee et al; "Biodegradable Implants for Sustained Drug Release in the Eye"; Pharmaceutical Research; Oct. 2010; vol. 27, No. 10; pp. 2043-2053.

* cited by examiner

*Primary Examiner* — Kami A Bosworth
*Assistant Examiner* — William Frehe
(74) *Attorney, Agent, or Firm* — Rosenberg, Klein & Lee

(57) ABSTRACT

A bioresorbable drug eluting intravitreal implant system includes a syringe with a chamber containing a medicinal drug. A balloon is releasably secured to a needle where the needle has a central section chamber in fluid communication with a chamber in the syringe. The needle central section has an opening formed through a wall for transporting the medicinal drug to the interior of the balloon subsequent to insertion of the needle through the sclera of a patient's eye.

7 Claims, 6 Drawing Sheets

BIORESORBABLE DRUG ELUTING INTRAVITREAL IMPLANT SYSTEM AND METHOD

REFERENCE TO RELATED PATENT APPLICATIONS

This patent application is Based upon Provisional Patent Application Ser. No. 61/901,099 filed at the uspto on 7 Nov. 2013.

FIELD OF THE INVENTION

The subject system and method is directed to treatment systems and methods for treating a multiplicity of eye diseases. The subject system and method relates to both devices and methods for treating patient's eyes having eye disorders or diseases and more particularly, to devices and methods for administering a therapeutic medium, medicinal drug or other agent into the vitreous cavity of a patient.

Still further, the subject system and method administers the therapeutic or medicinal agents to the tissues of the eye so that the pharmacodynamic action of the medicinal drugs may be localized at the choroid and the retina.

Still further, the subject system and method is directed through the use of a drug-eluting bioresorbable intravitreal implant through which therapeutic agents are administered intravitreally and can diffuse through the tissues of the eye over an extended period of time to localize the action of the therapeutic medium at the choroid, retina, ciliary body or any other layer of the eye.

BACKGROUND OF THE INVENTION

Numerous eye diseases may permanently damage vision in an effected eye or eyes and possibly lead to blindness if untreated. The subject system and method is directed to treating a wide number of vision-threatening disorders or diseases of the eye, including but not limited to, diseases of the retina, retinal pigment epithelium and choroid. Such vision threatening diseases include, for example, ocular neovascularization, ocular inflammation, and retinal degeneration.

PRIOR ART

Prior art treatments of various diseases of the eye have been previously treated by injection directly through the sclera of a medicinal drug composition. Such prior art systems and methods limit the effective delivery of therapeutic media to the retina/choroid when they are injected directly into the vitreous. Such systems and methods do not provide for a sustained therapy for the target tissue. Thus, there is a long felt need for a drug eluting intravitreal implant system which will permit the controlled eluting of the medicinal drug over an extended period of time.

Additionally, in such prior art procedures, does not permit the maintenance of the medicinal drug in a relatively stable position within the vitreous and may produce side effects associated with the injection of drugs directly.

SUMMARY OF THE INVENTION

Figure 1:
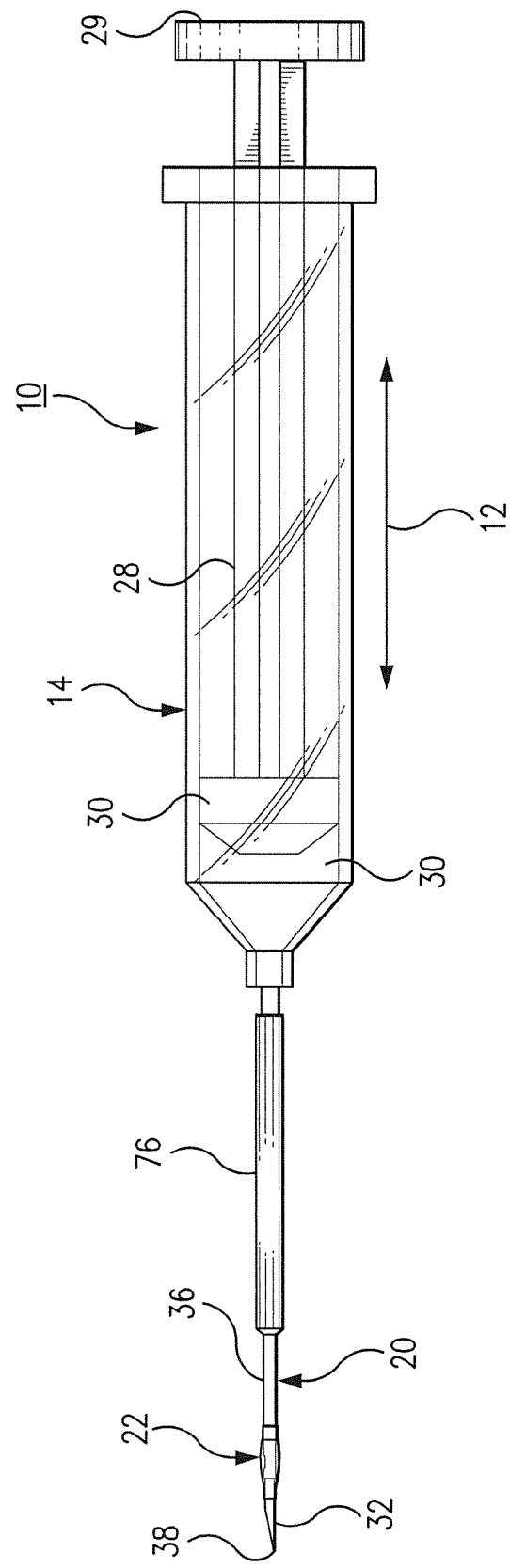
FIG. 1 is an elevational view of the bioresorbable intravitreal implant system.

In summary, the subject implant system and method of operation is for administering or delivering a therapeutic medium to an interior segment of a patient's eye where the therapeutic medium includes, but is not limited to, drugs, medicaments, antibiotics, antibacterials, antiproliferatives, neuraprotectives, anti-inflammatories (steroidal and non-steroidal), growth factors, neurotropic factors, antiangiogenics, thromobolytics, antibodies, biologics or genes.

The subject implant system and method provides for methods for the treatment and prevention of disorders or diseases of the eye, in particular, retinal/choroidal disorders or diseases through intravitreal administration or intravitreal prophylactic administration of such a therapeutic medium.

Such devices and methods according to the present invention include instilling or disposing of a therapeutic amount of therapeutic medium intravitreally or into the intravitreal space and more specifically, to localize the action of the therapeutic medium at the choroid and the retina of the eye.

The bioresorbable drug eluting intravitreal implant system of the subject system includes a syringe with a chamber adapted to contain a medicinal drug. The syringe has a displaceable plunger for transporting the medicinal drug external to the syringe from a syringe chamber containing the medicinal drug or other therapeutic agent. A needle includes or is formed into a distal end section, a central section, and a proximal section. A balloon member is releasably secured to the needle distal end section and the needle proximal section. The needle central section has a central section chamber in fluid communication with the syringe chamber with the needle central section having an opening formed through a wall for transport of the medicinal drug to an interior section of the balloon.

The concept also includes the method of implanting a bioresorbable drug into the eye of the patient by establishing a balloon shaped member having both a proximal and a distal end. The balloon shaped member includes a through opening extending from the proximal end to the distal end. The balloon shaped member is mounted over a needle member which in itself is formed of a distal section, a central section, and a proximal section. The balloon shaped member is in releasable contact with the distal end section and the proximal section of the needle shaped member. The needle member is then inserted through the sclera of a patient's eye to a predetermined depth and the balloon shaped member is inflated with a medicinal drug transported from a syringe through a flow channel into a central section chamber and through an opening formed through the needle central section to inflate the balloon shaped member with the medicinal drug.

The balloon shaped member may be formed into an ellipsoidal or spheroidal contour subsequent to inflation of the medicinal drug for placement into the vitreous cavity of the patient's eye. The ellipsoidal or somewhat spheroidal contouring of the balloon shaped member provides for a more stable positioning of the balloon shaped member in the vitreous cavity and conforms to the vitreous cavity contour in an optimized manner. Subsequent to inflation of the balloon shaped member, the needle is then withdrawn from the interior of the patient's eye and the balloon shaped member may be maintained through suturing or some like technique.

An object of the subject concept is to provide a bioresorbable drug eluting intravitreal implant system into the vitreous cavity a of the eye which elutes the medicinal drug in a controlled manner over a period of time.

Another object of the subject concept is to provide an implant system where the medicinal drug is contained within an enclosure which is biodegradable.

A still further object of the subject concept is to provide an implant system which may be quickly inserted through the sclera of a patient's eye with a reduced time for the overall procedure being accomplished.

A further object of the subject concept is to provide an implant system which reduces any side effects which would be typically associated with the injection of drugs directly into the vitreous.

DESCRIPTION OF THE PREFERRED EMBODIMENTS

Referring now to FIGS. 1-6, there is shown bioresorbable drug eluting intravitreal implant system 10 hereinafter referred to as implant system 10. Implant system 10 is composed of syringe 14, needle member 20, and balloon 22 which will be described in following paragraphs. Syringe 14 may be a standard surgical syringe formed of a plastic composition, not important to the inventive concept as herein described, with the exception that it be operable to transport a medicinal drug into balloon 22 which is implanted within an internal portion of eye 26 seen in FIG. 6. Syringe 14 extends in longitudinal direction 12 as seen in FIG. 1. Plunger 28 includes syringe head 29 which is manually displaced by a surgeon during an implant procedure. A syringe chamber 30 contains a medicinal drug or other therapeutic agent to be used during a surgical procedure. In operation, plunger 28 is displaced in longitudinal direction 12 to create a force against the medicinal drug contained within syringe chamber 30 to force the medicinal drug to be transported external syringe 14, as will be described in following paragraphs. Thus, syringe 14 includes chamber 30 adapted to contain the medicinal drug in combination and uses a displaceable plunger 28 for transmission of the medicinal drug from syringe 14.

Figure 3:
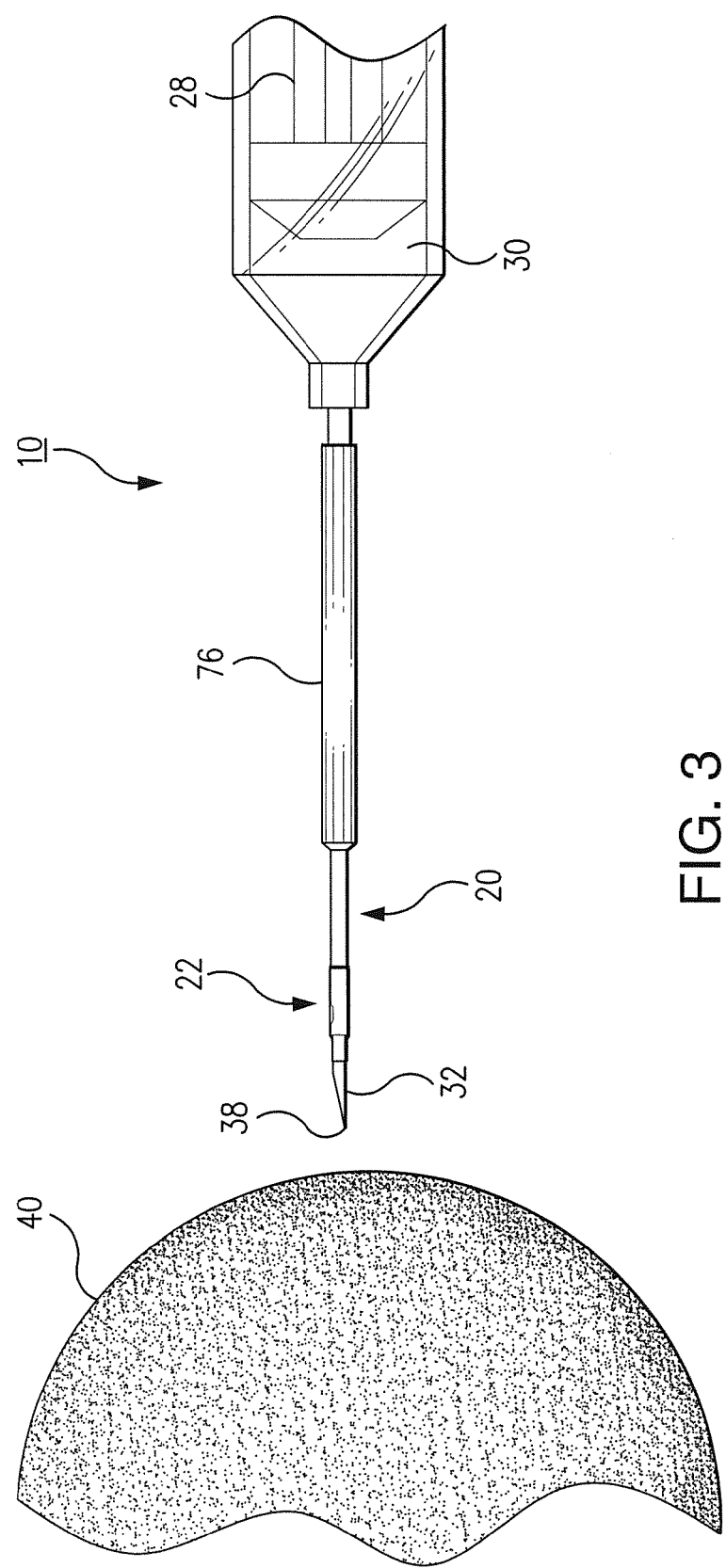
FIG. 3 is an elevational view in part of the bioresorbable drug eluting intravitreal implant system prior to insertion through the sclera of a patient's eye.
Figure 4:
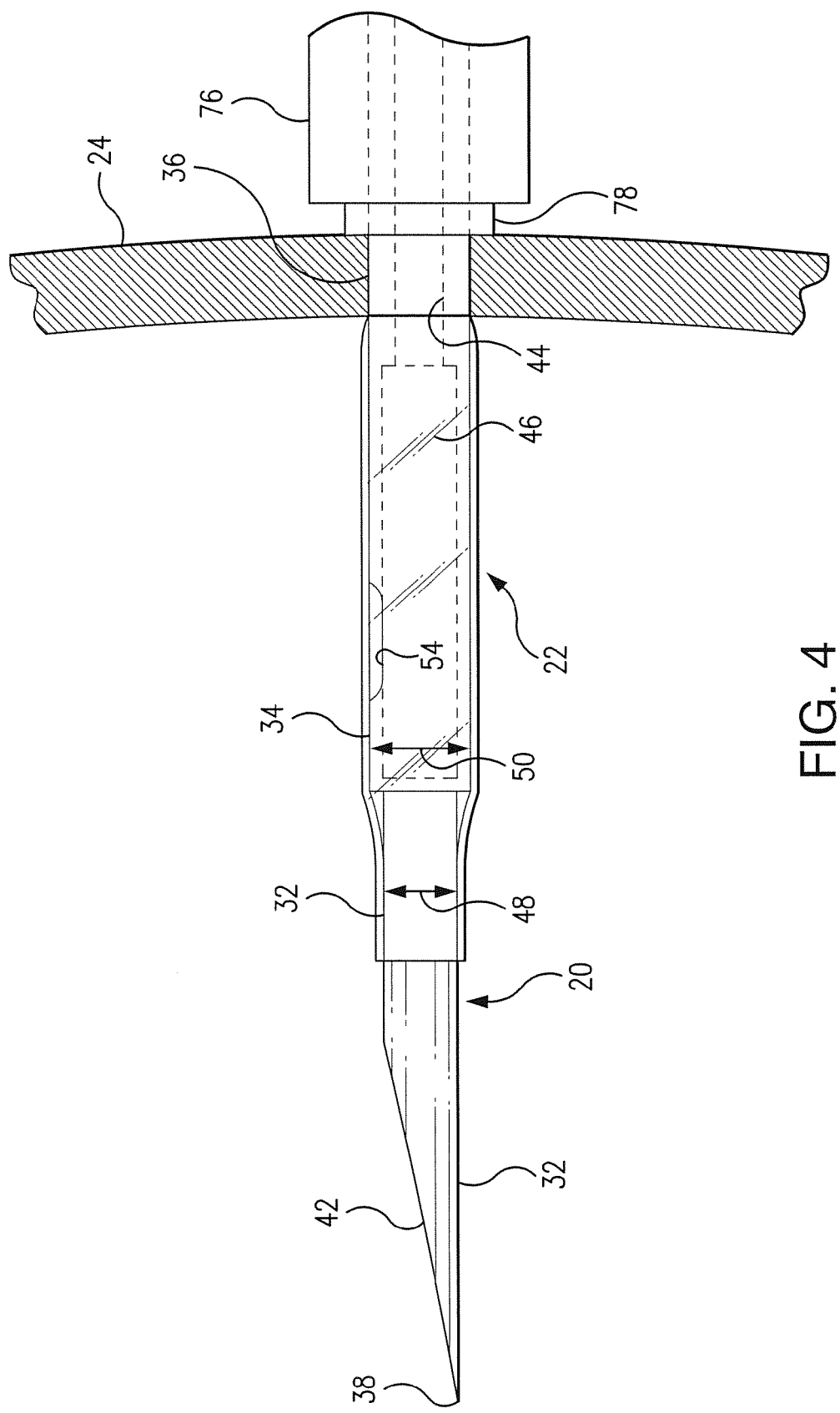
FIG. 4 is a cross-section of the implant system when inserted into the interior of the patient's eye prior to inflation of a balloon containing a therapeutic medium.
Figure 5:
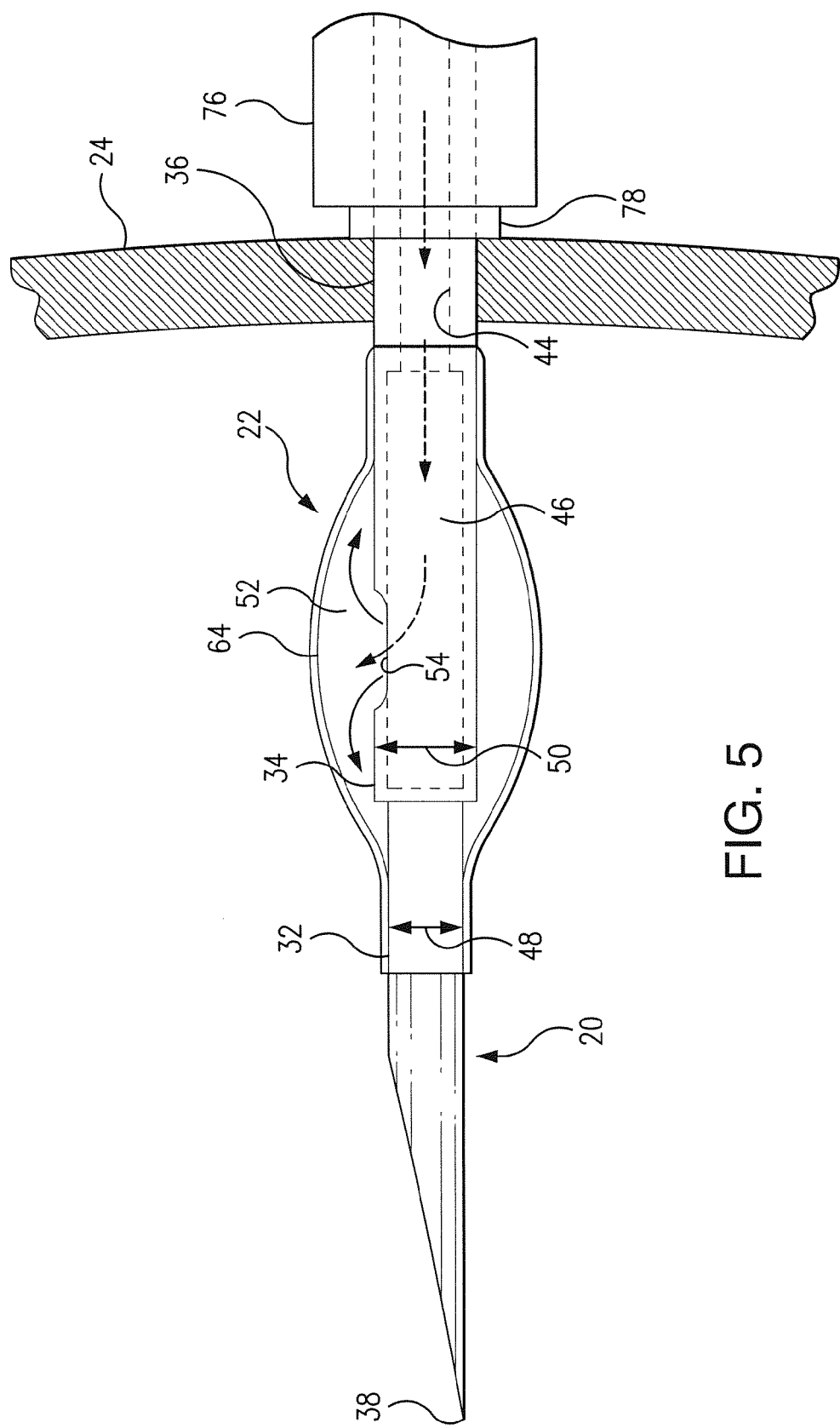
FIG. 5 is a cross-sectional view of a portion of the implant system showing the inflation of the balloon with the medicinal drug prior to removal of the needle from the interior of the patient's eye.

Needle 20 as more clearly seen in FIGS. 4 and 5, includes needle distal section 32, needle central section 34, and needle proximal section 36. Needle 20 includes needle point 38 formed on one end of needle distal section 32. As seen in FIG. 3, during the surgical procedure, needle 20 is inserted through sclera 24 of eye 40 to serve as a transport medium for balloon 22 to permit placement of the balloon 22 into interior 26 of the patient's eye 40, as will be detailed in following paragraphs. The diameter of needle distal section 32 is formed as small as possible for insert through sclera 24 but of sufficient diameter for transport and placement of balloon 22 into the vitreous cavity of the patient's eye 40. Needle distal section 32 includes a tapered section 42 for ease of passage through sclera 24 to the internal portion of eye 26.

In overall concept, needle 20 formed of needle distal section 32, needle central section 34, and needle proximal section 36, is used as the basic transporting mechanism for introducing balloon 22 into the internal portion 26 of eye 40.

Needle distal section 32 is formed somewhat in a rod-like construction and contains no through opening.

As is further shown in FIGS. 4 and 5, proximal section 36 and needle central section 34 include a flow channel 44 for insert of a medicinal drug into needle central section chamber 46 for transport of the medicinal drug internal to balloon 22, as is seen in FIG. 5. The needle distal section 32 has a diameter 48 which is less than the needle central section diameter 50. In this manner, a shoulder is created between needle distal section 32 and needle central section 34, as is seen in FIGS. 4 and 5.

In this manner, as plunger 28 is displaced in longitudinal direction 12, the medicinal drug contained within syringe chamber 30 is transported through flow channel 44 into needle central section chamber 46 as shown in FIG. 4 and is adapted to be further transported to an interior section 52 of balloon 22, as is seen in FIG. 5. In order to provide fluid communication from needle central chamber 46 to the interior 52 of balloon 22, an opening 54 is formed in a wall of needle central section 34, as is seen in FIG. 5.

Thus, medicinal drug is transported from syringe chamber 30 through flow channel 44 into needle central section chamber 46 and exits from opening 54 into the interior 52 of balloon 22, as is seen in FIGS. 4-5.

Figure 2:
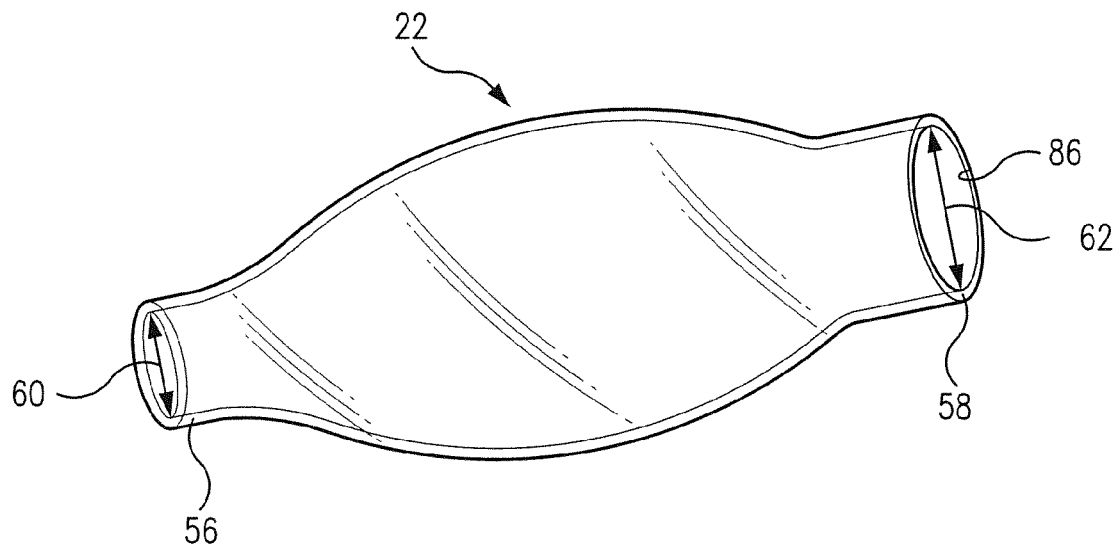
FIG. 2 is a perspective view of a balloon containing a medicinal drug.

Balloon 22 is mounted over needle central section 34 and needle distal section 32. In order to accommodate the mounting of balloon 22 on the needle distal section 32 and needle central section 34, balloon 22 has opposing distal end 56 and proximal end 58, as is seen in FIG. 2. Balloon distal end inner diameter 60 is less than the balloon proximal end inner diameter 62 to permit accommodation of mounting of balloon proximal end 58 on needle central section 34 and needle proximal section 36 while permitting mounting of balloon distal end 56 on needle distal section 32. Balloon or balloon shaped member 22 is shown in FIG. 2 in at least a partially inflated state for illustrative purposes for explanation of the sizing of balloon 22.

Balloon 22 is formed of a substantially elastic and biodegradable composition which will be absorbed into the patient subsequent to implantation of balloon 22 within the internal portion of eye 26 subsequent to the procedure.

In the deflated condition of balloon 22, as is seen in FIGS. 1 and 4, balloon 22 is mounted over needle distal section 32 and needle central section 34 where balloon 22 is substantially flush with and abuts needle central section 34, needle distal section 32, and needle proximal section 36. Subsequent to insertion of needle 22 through sclera 24, balloon 22 is inflated with the medicinal drug, as is seen in FIG. 5, prior to removal of needle 22 from the internal portion of eye 40.

Figure 7:
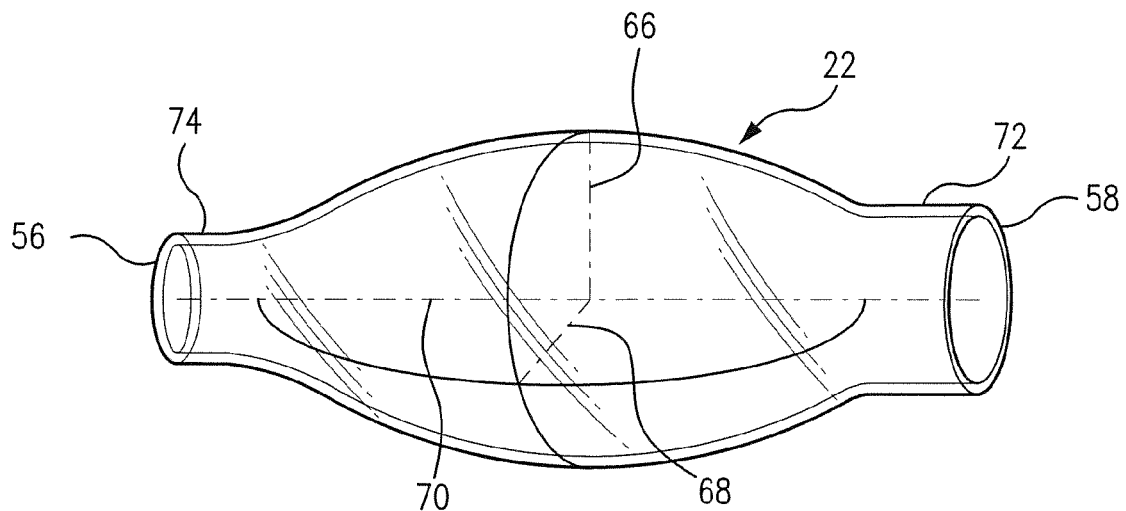

Opening or slot 54 formed in needle central section 34 is seen to be in alignment with balloon central section 64 as shown in FIG. 5 to allow transport of the medicinal drug from needle central section chamber 46 into the interior 52 of balloon 22. In a preferred embodiment, as seen in FIG. 7, when inflated, balloon 22 assumes an ellipsoidal/spheroidal contour for optimization of placement in the interior portion 26 of eye 40. Balloon 22 includes proximal neck section 72 and distal neck section 74. When inflated, the balloon Z-axis radius 66 would approximate 3.0 mm, the balloon Y-axis radius 68 would approximate 3.0 mm with the longitudinal or X-axis radius 70 approximating 4.0 mm. This would provide for an approximate internal volume of balloon 22 to be substantially 150 mm$^3$. This optimum type of configuration is seen in FIG. 7 which provides for an optimization of the eluting drug from internal balloon 22 subsequent to insertion into interior 26 of eye 40. Once inserted, medicinal drug is eluted from both balloon distal end 56 and balloon proximal end 58 in a controlled manner to provide therapeutic value to the patient over an extended period of time.

Figure 6:
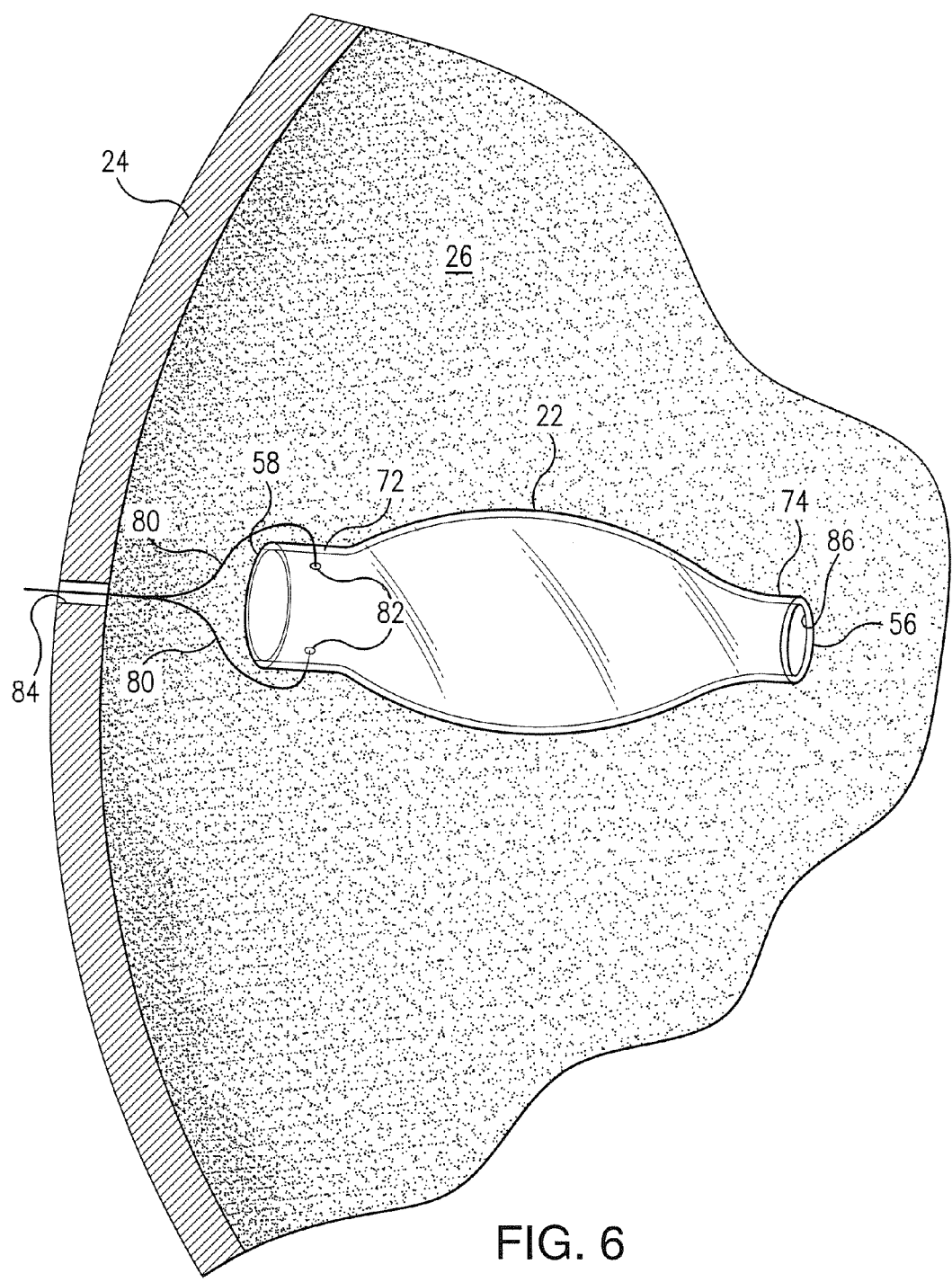
FIG. 6 is a schematic representation partially in perspective of a balloon within the eye of the patient being secured by sutures; and, FIG. 7 is a schematic representation of the balloon member showing dimensional characteristics for an ellipsoidal/spheroidal contour of the balloon.

Implant system 10 further includes sleeve member 76 which is slidably received on needle proximal section 36 to aid in the removal of needle 20 from the interior 26 of eye 40. In this manner, the surgeon may grasp sliding sleeve 76 and simply pull syringe 14 including needle 20 from the interior 26 of eye 40 while maintaining balloon 22 containing the medicinal drug within interior 26, as is seen in FIG. 6.

Fixing member or stop member 78 is secured to an end of proximal end section 36. Stop member 78 has an external diameter greater than an outer diameter of needle proximal section 36 and less than an outer diameter of slidable sleeve member 76. In this manner, the depth of balloon 22 within the interior 26 of eye 40 may be controlled to ensure that balloon 22 is accurately positioned during the procedure. Compositions of sliding sleeve 76 and stop member 78 are not important to the inventive concept of the subject implant system 10, with the exception that they be compatible with surgical room procedure requirements.

In some instances, balloon 22 filled with the medicinal drug may be left within interior 26 of eye 40. However, in a preferred embodiment, balloon 22 is somewhat fixedly positioned within interior 26 by sutures 80, as seen in FIG. 6. Sutures 80 are fixed to balloon proximal end section 72 at suture fixing points 82 and extend through sclera slit 84 (enlarged for purposes of illustration) formed by the needle 20 upon insert through sclera 24. In this manner, medicinal drug 22 may be positionally located in a somewhat stable manner within interior 26 of eye 40. Medicinal drug is eluted to the interior 26 through the open balloon distal end 56 and balloon proximal end 58. Balloon 22 being formed of a biodegradable composition essentially works its way into the body of the patient subsequent to the medicinal drug being dispersed over a period of time.

FIGS. 1-6 are descriptive of a method of implanting a bioresorbable drug into the eye 40 of a patient. Initially, a balloon shaped member 22 formed of a biodegradable composition is established with the balloon shaped member 22 having a proximal end 58 and a distal end 56. The balloon-shaped member 22 has a through opening 86 extending throughout the balloon length from the balloon distal end 56 to the balloon proximal end 58. The balloon shaped member 22 is mounted over needle 20 having a distal end section 32, a central section 34, and a needle proximal section 36. Balloon shaped member 22 is mounted in releasable contact with needle distal end section 32 and needle proximal section 36. Prior to insertion of needle 20 through sclera 24, balloon shaped member 22 is snugly mounted to and is substantially in contiguous contact throughout its length with needle distal section 32 and needle central section 34 as well as needle proximal section 36.

Needle member 20 is then inserted through sclera 24 of eye 40 to a predetermined depth. Balloon shaped member 22 is then inflated with the medicinal drug being transported from needle central section 34 to the interior 52 of balloon shaped member 22. Balloon shaped member 22 assumes a somewhat ellipsoidal/spheroidal contour, as is seen in FIGS. 2 and 7, as was previously described. Needle 20 is then withdrawn from interior 26 of eye 40 and balloon shaped member 22 is positioned within the patient's eye 40. The medicinal drug transport mechanism for inflation of balloon shaped member 22 is by actuation of plunger 28 of syringe 14 in longitudinal direction 12 to transport the medicinal drug within syringe chamber 30 through flow channel 44, opening or slot 54 into the interior 52 of balloon shaped member 22.

Balloon shaped member 22 may be maintained within interior 26 by sutures 80 which are attached to balloon proximal neck section 72 and extend through sclera 24, as is seen in FIG. 6. In this manner, balloon shaped member 22 is maintained at a relatively stable position within interior 26. In other embodiments, balloon shaped member 22 may be left in a somewhat free-floating manner within the vitreous cavity thus negating the use of fixing mechanisms for the balloon 22 within the eye 40.

Although this invention has been described in connection with specific forms and embodiments thereof, it will be appreciated that various modifications other than those discussed above may be resorted to without departing from the spirit or scope of the invention as defined in the appended claims. For example, functionally equivalent elements may be substituted for those specifically shown and described, certain features may be used independently of other features, and in certain cases, particular locations of elements, steps, or processes may be reversed or interposed, all without departing from the spirit or scope of the invention as defined in the appended claims.

What is claimed is:

1. A method of implanting a bioresorbable drug into an eye of a patient including the steps of:

(a) establishing a balloon shaped member having a proximal end and a distal end, said balloon shaped member having a through opening extending from said proximal end to said distal end thereof, wherein said balloon shaped member has an unexpanded configuration and an expanded configuration;

(b) establishing a needle member with a closed distal section, a proximal section, and a central section therebetween, forming a central section chamber defined by walls of said needle member at said central section thereof, and forming at least one opening through said walls of said needle member at said central section thereof, wherein said central section chamber has a distal wall positioned in proximity to said distal section of said needle member to block a fluid communication between said central section chamber and said distal section of said needle member, releasably mounting said balloon shaped member, in its unexpanded configuration, in alignment with said at least one opening, over said needle member with said distal and proximal ends of said balloon shaped member in releasable contact with said closed distal section and said proximal section of said needle member, respectively;

(c) inserting said needle member, carrying said balloon shaped member in said unexpanded configuration, through the sclera of the patient's eye to a predetermined depth;

(d) subsequently to inserting said needle member to a desired location in the patient's eye, inflating said balloon shaped member with a medicinal drug transported from said central section chamber formed in said needle central section to an interior of said balloon shaped member through said at least one opening formed through the walls of said central section of said needle member;

(e) subsequently to inflating said balloon member with said medicinal drug, withdrawing the needle member from the expanded balloon member and from interior of the patient's eye; and (f) maintaining said expanded balloon shaped member within the patient's eye.

2. The method as recited in claim 1 where the step of inflating said balloon shaped member includes the step transporting said medicinal drug from said needle central section to an interior of said balloon shaped member.

3. The method as recited in claim 2 where the step of transporting said medicinal drug includes the step of forming a needle central section chamber in fluid communication with said interior of said balloon shaped member.

4. The method as recited in claim 1 where the step of establishing said balloon shaped member includes the step of forming said proximal end with an internal diameter larger than an internal diameter of said distal end.

5. The method as recited in claim 1 where said balloon shaped member is formed of a biodegradable composition.

6. The method as recited in claim 1 where the step of mounting said balloon shaped member includes the step of positionally locating a central section of said balloon shaped member over said central section of said needle member.

7. The method as recited in claim 1 where the method of maintaining said balloon shaped member includes the step of suturing said balloon shaped member to the eye of the patient.

* * * * *